(12) United States Patent
Hattori et al.

(10) Patent No.: US 7,871,754 B2
(45) Date of Patent: Jan. 18, 2011

(54) PHOTOSENSITIVE COMPOSITION

(75) Inventors: Shigeki Hattori, Kawasaki (JP); Satoshi Saito, Yamato (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 331 days.

(21) Appl. No.: 12/191,517

(22) Filed: Aug. 14, 2008

(65) Prior Publication Data

US 2009/0208866 A1 Aug. 20, 2009

(30) Foreign Application Priority Data

Feb. 19, 2008 (JP) ............................. 2008-037892

(51) Int. Cl.
*G03F 7/004* (2006.01)
*G03F 7/30* (2006.01)

(52) U.S. Cl. ..................... 430/270.1; 430/326; 430/330

(58) Field of Classification Search .............. 430/270.1, 430/326, 330
See application file for complete search history.

(56) References Cited

U.S. PATENT DOCUMENTS

| | | | |
|---|---|---|---|
| 5,637,669 A * | 6/1997 | Hefner et al. ................. 528/97 |
| 6,197,473 B1 | 3/2001 | Kihara et al. |
| 7,241,554 B2 | 7/2007 | Saito |
| 7,338,755 B2 | 3/2008 | Saito |
| 7,361,451 B2 * | 4/2008 | Oshima et al. .............. 430/302 |
| 7,585,928 B2 * | 9/2009 | Hefner, Jr. ................... 528/86 |
| 2007/0059632 A1 * | 3/2007 | Oguro et al. ............. 430/270.1 |
| 2007/0224550 A1 | 9/2007 | Saito |
| 2007/0238050 A1 | 10/2007 | Saito |
| 2009/0081582 A1 | 3/2009 | Hattori et al. |

FOREIGN PATENT DOCUMENTS

JP 2003-261473 9/2003

OTHER PUBLICATIONS

Tomonari Nakayama, et al., "A Negative-Working Alkaline Developable Photoresist Based on Calix[4]resorcinarene, a Cross-linker, and Photoacid Generator", Chemistry Letters, 1997, pp. 265-266.
Toshiaki Kadota, et al., "Novel Electron-Bean Molecular Resists with High Resolution and High Sensitivity for Nanometer Lithography",Chemistry Letters, 2004, vol. 33, No. 6, pp. 706-707.
Oscar De Frutos, et al., "Synthesis and Self-Association of syn-5,10,15-Trialkylated Truxenes", Chemistry—A European Journal, vol. 8, No. 13, 2002, pp. 2879-2890.
Oscar De Frutos, et al., "syn-Trialkylated Truxenes: Building Blocks That Self-Associate by Arene Stacking", Angewandte Chemie International Edition, vol. 38, No. 1/2, pp. 204-207.
* cited by examiner

*Primary Examiner*—John S Chu
(74) *Attorney, Agent, or Firm*—Oblon, Spivak, McClelland, Maier & Neustadt, L.L.P.

(57) ABSTRACT

A photosensitive composition is provided, which includes a compound expressed by the formula T3 and a photo-acid generator which generates an acid by an action of actinic radiation. In the formula T3, $R^3$s are hydrogen atoms and hydrophobic groups. The hydrophobic groups are selected from the group consisting of (AD-1), (AD-2), and (AD-3) shown below, and the hydrogen atoms are partially substituted with a hydrophilic group (LA) shown below.

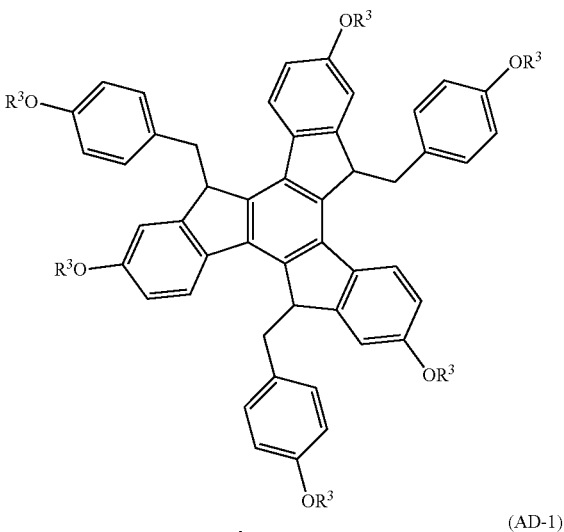

formula T3

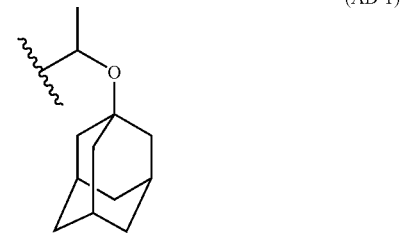

(AD-1)

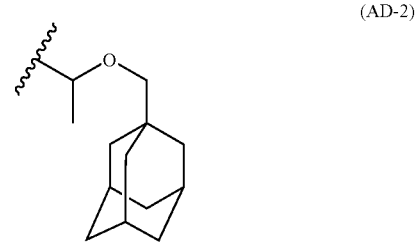

(AD-2)

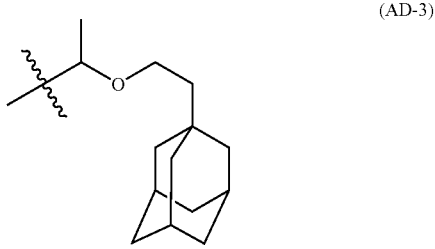

(AD-3)

(LA)

20 Claims, No Drawings

PHOTOSENSITIVE COMPOSITION

CROSS-REFERENCE TO RELATED APPLICATIONS

This application is based upon and claims the benefit of priority from prior Japanese Patent Application No. 2008-037892, filed Feb. 19, 2008, the entire contents of which are incorporated herein by reference.

BACKGROUND OF THE INVENTION

1. Field of the Invention

The present invention relates to a photosensitive composition used in microfabrication in a process for producing semiconductor elements, etc. and a method for forming a pattern with the same.

2. Description of the Related Art

In the trial production of microwave devices and quantum effect devices, fine patterning of 100 nm or less is required. In the case where a polymer compound is contained in a resist, the molecular size of the compound tends to affect edge roughness and other properties. Therefore, it is difficult to improve the resolution of a resist composed mainly of a polymer compound.

In order to achieve a high resolution, EB resists composed of cyclic phenol derivatives have been studied. However, there is still no resist having a high resolution and a sufficient sensitivity, and being developable with an aqueous alkaline solution.

For example, alkali-soluble cyclic phenol derivatives such as a negative resist comprising cyclic resorcinol and a positive resist comprising a phenyl derivative are proposed in Chem. Lett. 1997 (3), 265 and Chem. Lett. 2004 (6), 706. However, these resists cannot form satisfactory patterns, and are not examined as to adhesion to substrates.

In addition, truxene derivatives as low molecular weight compounds having high heat resistance are proposed in JP-A 2003-261473(KOKAI). However, no specific method has been disclosed for using the truxene derivatives as photosensitive compositions for pattern formation.

BRIEF SUMMARY OF THE INVENTION

A photosensitive composition according to one aspect of the present invention comprises:
a compound expressed by the formula T1:

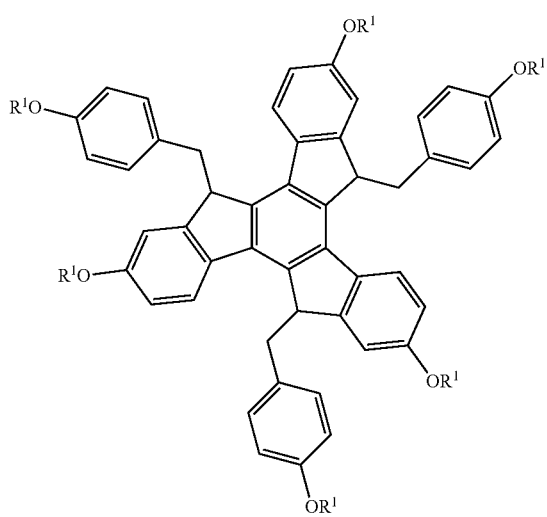

formula T1 wherein $R^1$s are hydrogen atoms, and are partially substituted with hydrophobic groups, the hydrophobic groups being at least one selected from the group consisting of AD-1, AD-2, and AD-3 shown below; and

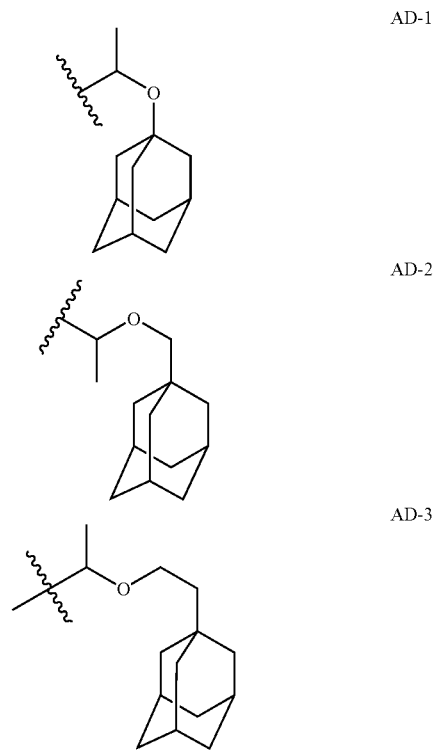

a photo-acid generator which generates an acid by an action of actinic radiation.

A photosensitive composition according to another aspect of the present invention comprises:
a compound expressed by the formula T2:

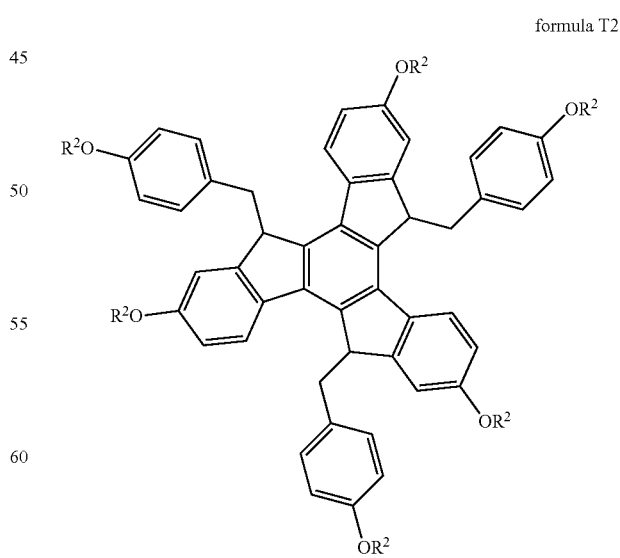

formula T2 wherein $R^2$s are hydrogen atoms, and are partially substituted with a hydrophilic group LA shown below; and

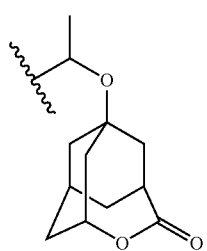

a photo-acid generator which generates an acid by an action of actinic radiation.

A photosensitive composition according to another aspect of the present invention comprises:

a compound expressed by the formula T3:

formula T3

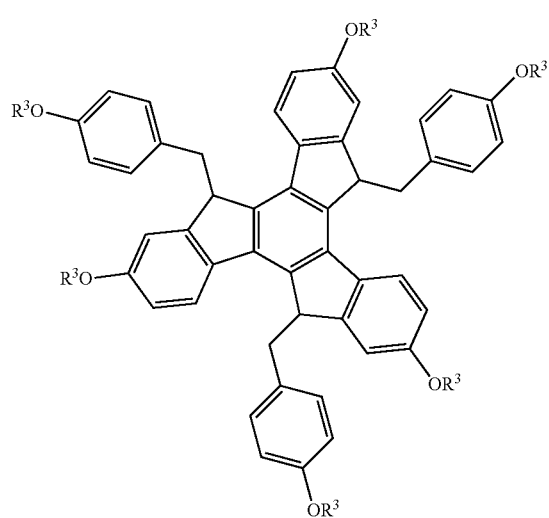

wherein $R^3$s are hydrogen atoms and hydrophobic groups, the hydrophobic groups being selected from the group consisting of AD-1, AD-2, and AD-3 shown below, the hydrogen atoms being partially substituted with a hydrophilic group LA shown below; and

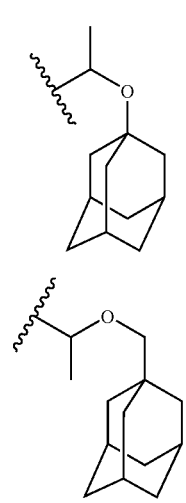

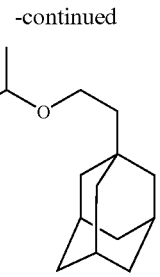

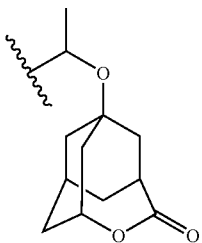

a photo-acid generator which generates an acid by an action of actinic radiation.

A method for forming a pattern according to one aspect of the present invention comprises:

forming a photosensitive layer containing the aforementioned photosensitive composition above a substrate;

subjecting a predetermined region of the photosensitive layer to pattern exposure by irradiation with actinic radiation;

subjecting the substrate to a heat treatment; and subjecting the photosensitive layer after the heat treatment to a development treatment with an alkali aqueous solution, to selectively remove the light-exposed portion of the photosensitive layer.

DETAILED DESCRIPTION OF THE INVENTION

Embodiments will be described below.

The photosensitive composition according to one embodiment has a truxene structure, and contains a compound having a specific acid-leaving group (hereinafter referred to as a truxene derivative), and a photo-acid generator which generates an acid by an action of actinic radiation. The truxene derivative is expressed by the formula (T1), (T2), or (T3).

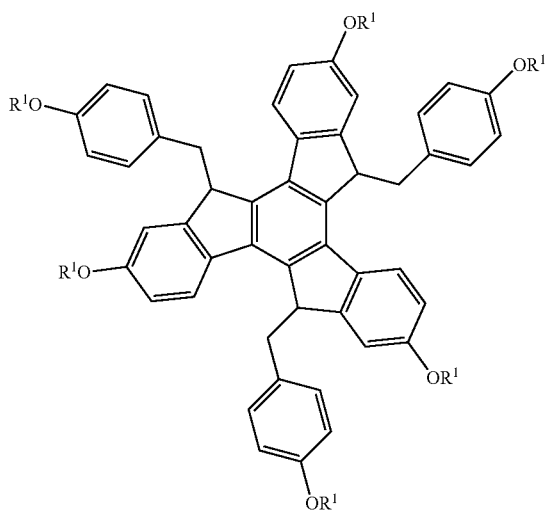

-continued

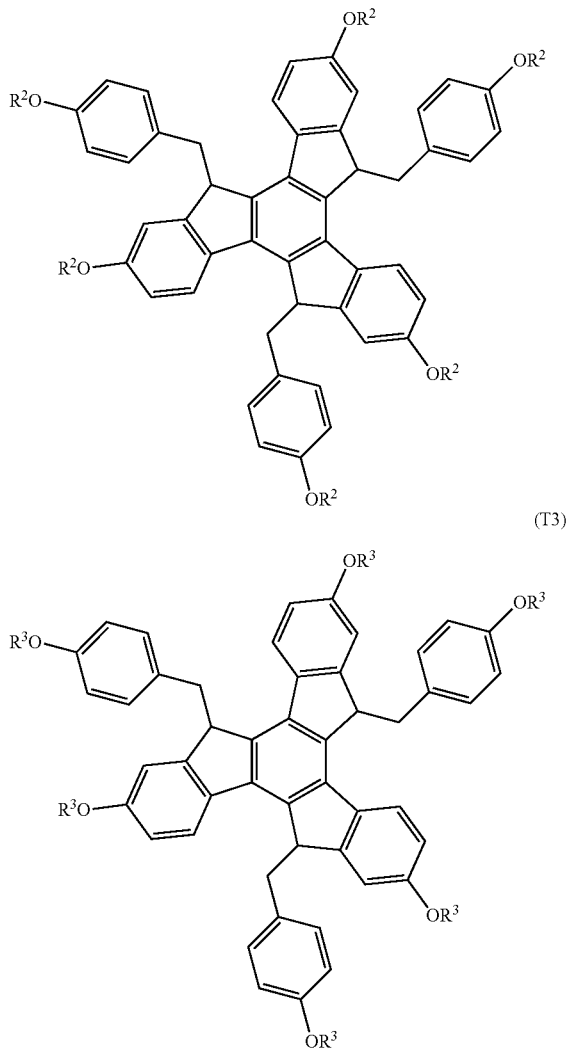

(T2)

(T3)

In the formula (T1), R¹s are hydrogen atoms, and are partially substituted with at least one hydrophobic group selected from the group consisting of (AD-1), (AD-2), and (AD-3) shown below. In the formula (T2), R²s are hydrogen atoms, and are partially substituted with the hydrophilic group (LA) shown below. In the formula (T3), R³s are hydrogen atoms and hydrophobic groups. The hydrophobic groups are selected from the group consisting of (AD-1), (AD-2), and (AD-3) shown below, and the hydrogen atoms are partially substituted with the hydrophilic group (LA) shown below. All of is these hydrophobic groups and hydrophilic groups are acid-leaving groups.

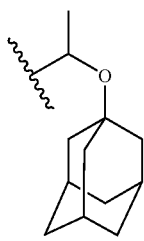

(AD-1)

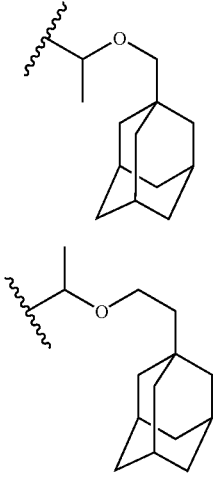

(AD-2)

(AD-3)

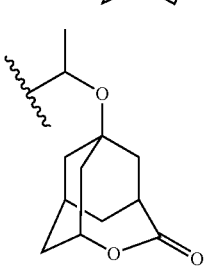

(LA)

When a specific region of a photosensitive layer including the photosensitive composition is irradiated with actinic radiation, an acid is generated from the photo-acid generator selectively in the exposed region. The truxene derivative used in the embodiment has an acid-leaving group which is decomposed by an acid. Accordingly, the exposed region of the photosensitive layer becomes more soluble in an aqueous alkaline solution, and thus can be selectively removed through dissolution in an alkaline developing solution. More specifically, the photosensitive composition according to the embodiment is a chemically amplified positive resist.

The compounds expressed by the formulas (T1), (T2), and (T3) are contained in the photosensitive composition as matrix compounds. These compounds have a highly rigid truxene structure at the center. In the truxene structure, aromatic rings are stereoscopically immobilized by five-membered rings. Therefore, the structure is highly rigid, suppresses entropy change, and thus exhibits high heat resistance.

In addition, benzil groups are bonded to the 5, 10, and 15 positions in the truxene structure, and the three benzil groups increase the amorphousness.

All of the compounds expressed by the formulas (T1), (T2), and (T3) are low molecular weight compounds. In general, a low molecular weight compound exhibits crystallinity and does not exhibit amorphousness. However, the compounds expressed by the formulas (T1), (T2), and (T3) exhibit exceptional amorphousness. The inventors have found that these compounds have favorable properties as matrix compounds.

The photosensitive composition according to one embodiment contains a low molecular weight compound having a small molecular size as a matrix compound. Therefore, the photosensitive composition is composed exclusively of compounds having low molecular weights. As a result, the photosensitive composition exhibits improved resolution and edge roughness.

For example, a polymer compound has a large molecular size, so that the assembly having a network structure composed of entangled molecular chains has a large size. In the case where the polymer compound is contained as a matrix compound in a photosensitive composition, large assemblies are detached from the exposed regions during development. The detachment results in large edge roughness on the side walls of the pattern formed by development.

On the other hand, a low molecular weight compound has a small molecular size, so that the assembly composed of entangled molecular chains has a small size. Therefore, in the case where a photosensitive composition is composed exclusively of low molecular weight compounds, small assemblies are detached from the exposed regions during development. Even if edge roughness occurs on the side walls of the pattern formed by development, the degree thereof is slight. Accordingly, the photosensitive composition according to the embodiment composed of low molecular weight compounds improves the resolution and edge roughness.

The photosensitive composition according to one embodiment contains a truxene derivative having a specific acid-leaving group, and thus improves the resolution and edge roughness, and achieves ultrahigh sensitivity.

The acid-leaving group preferably contains an acetal having the smallest bond cleavage energy during catalytic reaction of the acid generated from the photo-acid generator. An acetal is advantageous in readily causing the elimination reaction of the protecting group to improve the sensitivity.

In addition to an acetal, the acid-leaving group preferably further includes an alicyclic structure. Irradiation with actinic radiation in a vacuum causes degasification, which contaminates the inside of an irradiation device. The alicyclic structure prevents such a problem. More specifically, an alicyclic structure usually exhibits a high boiling point of 200° C. or higher, and thus prevents the occurrence of degasification. The alicyclic structure is not particularly limited, and particularly preferable examples thereof are adamantane and hyper-lactone.

Since adamantane is highly hydrophobic, it exhibits a high inhibitory effect against the developing solution at a low protection rate, and leaves many hydroxy groups. As a result, adhesion to the silicon substrate is kept high, and the contrast is improved. More specifically, the hydrophobic group containing adamantane is selected from the group consisting of (AD-1), (AD-2), and (AD-3).

Contrary to adamantane, hyper-lactone is hydrophilic, so that it keeps the surface energy of the resist film at a high level even with a high protection rate. More specifically, hyper-lactone improves the adhesion to a silicon substrate or the like while maintaining high contrast. Hyper-lactone is the above-described hydrophilic group (LA).

As described above, all of (AD-1), (AD-2), (AD-3), and (LA) contribute to improvement of the contrast.

In the formula (T1), the hydrophobic groups selected from (AD-1), (AD-2), and (AD-3) are introduced to some $R^1$s, and the other $R^1$s are hydrogen atoms. In consideration of dissolution inhibition against an aqueous developing solution and adhesion to a silicon substrate or the like, the hydrogen atoms preferably constitute 10 to 90% of the total number of $R^1$s. The proportion of the hydrogen atoms with respect to the total number of $R^1$s is the number average percentage calculated by dividing the number of $R^1$s having hydrogen atoms in all molecules by the total number of $R^1$s.

Assuming that the total number of molecules is 200, and hydrogen atoms are introduced to two $R^1$s in 100 molecules, and hydrogen atoms are introduced to four $R^1$s in the remaining 100 molecules; $2 \div 6 \times 100 + 4 \div 6 \times 100) \div 200 = 0.5$, so that 50% of the total number of $R^1$s are hydrogen atoms. For the below-described cases with $R^2$ and $R^3$, the proportion of hydrogen atoms with respect to the total amounts can be calculated by the same method.

The aqueous developing solution may be an alkaline developing solution such as a tetramethylammonium hydroxide aqueous solution, a tetraethylammonium aqueous solution, a choline aqueous solution, a potassium hydroxide aqueous solution, or a sodium hydroxide aqueous solution. The content of hydrogen atoms is more preferably 20 to 60% with respect to the total number of $R^1$s.

In the formula (T2), the hydrophilic group (LA) is introduced to some of $R^2$s, and the other $R^2$s are hydrogen atoms. For the above-described reason, the hydrogen atoms preferably constitute 10 to 90% of the total number of $R^2$s. The content of the hydrogen atoms is more preferably 60 to 80% with respect to the total number of $R^2$s.

In the formula (T3), a hydrophobic group selected from (AD-1), (AD-2), and (AD-3) and the hydrophilic group (LA) are introduced to some of $R^3$s, and the other $R^3$s are hydrogen atoms. For the above-described reason, the hydrogen atoms preferably constitute 10 to 90% of the total number of $R^3$s. The content of the hydrogen atoms is more preferably 40 to 80% with respect to the total number of $R^3$s.

The ratio between the hydrophobic and hydrophilic groups introduced into $R^3$ is preferably from 2:1 to 1:2. In this case, the above-described dissolution inhibition ability and adhesion can be strictly controlled. The ratio between the hydrophobic and hydrophilic groups is more preferably from 2:3 to 3:2, and most preferably 1:1.

Among the hydrophobic groups (AD-1), (AD-2), and (AD-3), (AD-3) most effectively inhibit dissolution in an aqueous developing solution, followed by (AD-2) and (AD-1) in this order. Therefore, it is most preferable that all the hydrophobic groups are (AD-3).

Decomposition of the acid-leaving group containing the hydrophobic group and/or hydrophilic group is caused by an acid generated from the photo-acid generator. The photo-acid generator is a compound which generates an acid by an action of actinic radiation. Actinic radiation specifically refers to ultraviolet radiation and ionizing radiation. The photo-acid generator is preferably sulfonyl, iodonium, or other onium salt compound or sulfonyl ester. Examples of the photo-acid generator include the following:

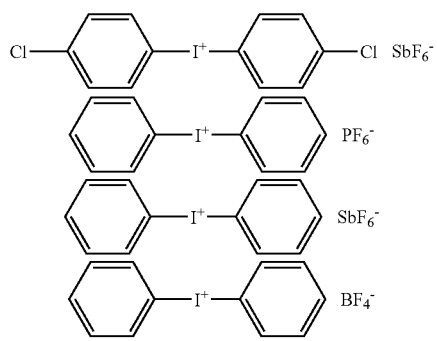

-continued
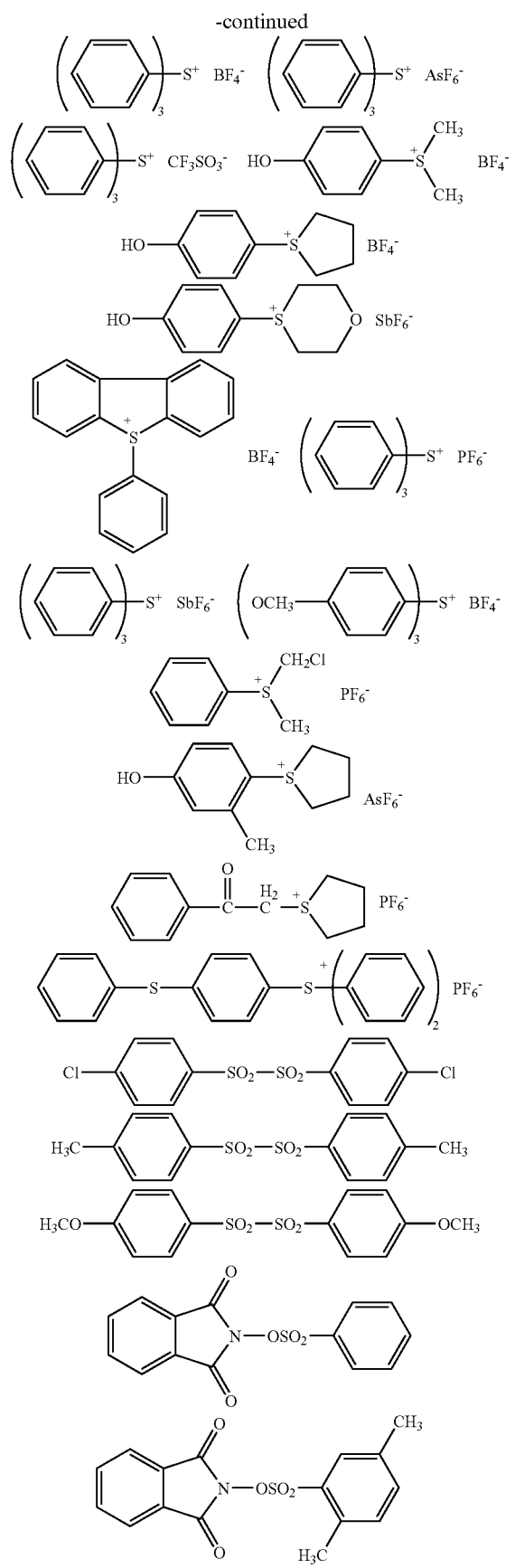
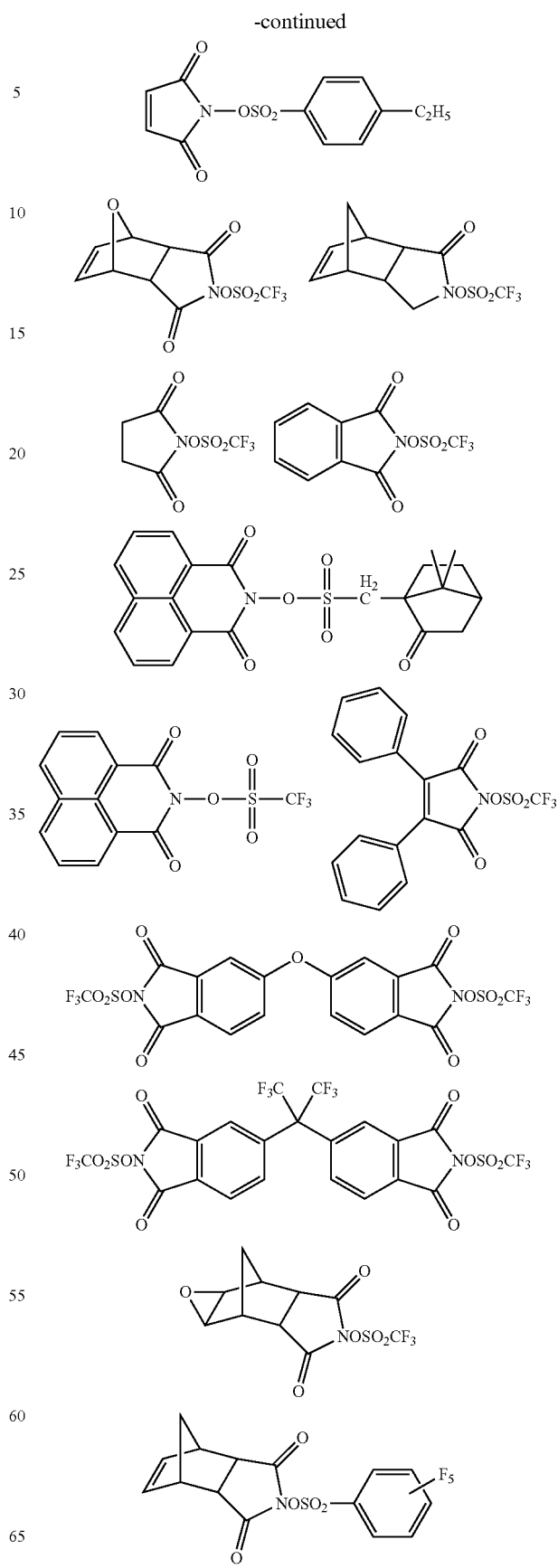

-continued

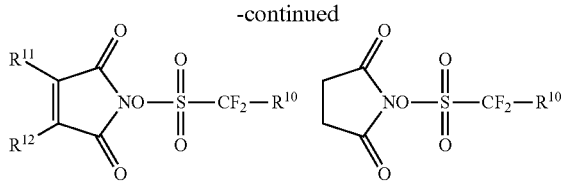

Wherein $R^{10}$, $R^{11}$, and $R^{12}$ may be the same or different from one another, and are selected from substituted or unsubstituted alkyl groups, and substituted or unsubstituted aryl groups;

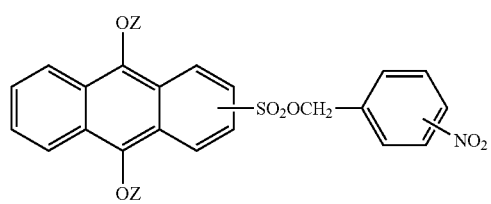

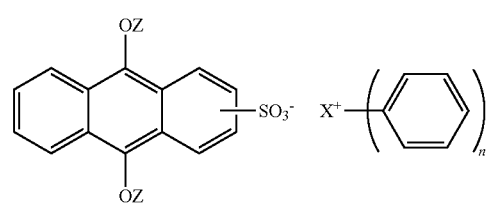

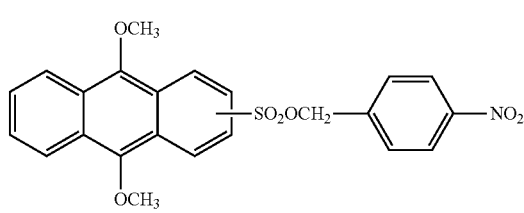

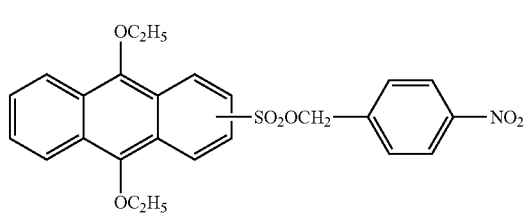

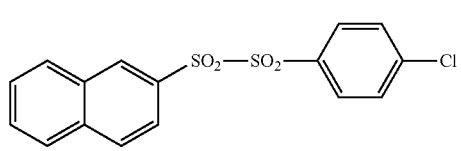

Wherein Z is a substituent selected from a substituted or unsubstituted alkyl group, a substituted or unsubstituted alkoxy group, a substituted or unsubstituted aryl group, and a halogen atom; $X^+$— is an arbitrary cationic group; n is an integer of 1 to 3 to make the total charge of the cationic group $+1$.

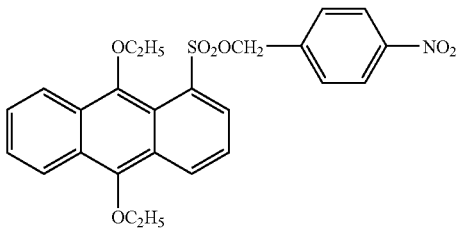

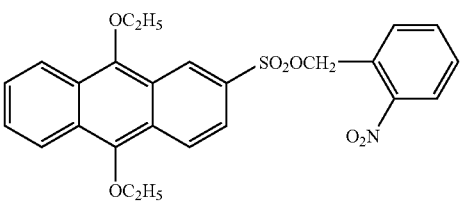

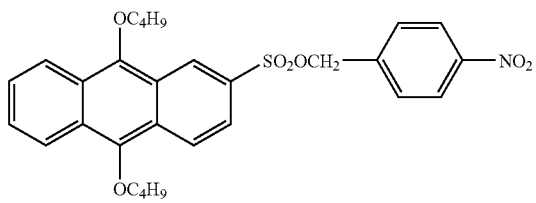

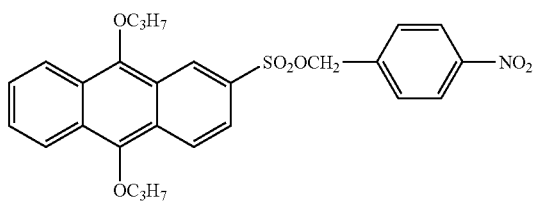

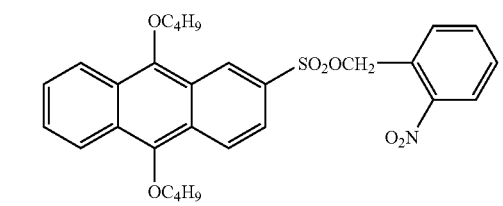

The photo-acid generator may be used alone or in combination of two or more thereof. The content of the photo-acid generator is commonly from 0.1 to 10.0% by weight with respect to the total weight of the solid content contained in the photosensitive composition. The solid content is determined by subtracting the organic solvent component from the photosensitive composition. If the content of the photo-acid generator is too low, it is difficult to achieve sufficient sensitivity. In particular, irradiation with ionizing radiation requires a greater amount of the photo-acid generator than ultraviolet radiation. On the other hand, if the content of the photo-acid generator is too high, for example, during exposure to ArF excimer laser beams, optical absorption by the photo-acid generator may impair the optical transparency of the photosensitive composition at the exposure wavelength. The content of the photo-acid generator is more preferably from 0.3 to 5.0% by weight with respect to the solid content.

The photosensitive composition according to the embodiment may contain various additives as necessary. For example, in order to reduce the influence of a basic compound in the environment, which is a disadvantage of a chemically amplified resist, a trace amount of the basic compound may be added.

Examples of the basic compound include pyridine derivatives, aniline derivatives, amine compounds, and indene derivatives. Examples of the pyridine derivatives include t-butylpyridine, benzilpyridine, and various pyridinium salts. Examples of the aniline derivatives include N-methylaniline, N-ethylaniline, and N,N'-dimethylaniline. Examples of the amine compounds include diphenylamine and N-methyldiphenylamine.

The content of the basic compound is preferably from 0.1 to 100 mol % with respect to the number of moles of the photo-acid generator. When the content is within the range, the effect of the basic compound is sufficiently achieved without excessively deteriorating the sensitivity of the photosensitive composition. The content of the basic compound is preferably adjusted according to the patterning apparatus, etc. to be used. The content of the basic compound is more preferably from 5 to 90 mol % with respect to the number of moles of the photo-acid generator.

The photosensitive composition according to the embodiment may be prepared by dissolving the above-described components in a solvent, followed by filtration through a membrane filter or the like. Examples of the solvent include organic solvents such as ketones, cellosolves, and esters. Examples of the ketone include cyclohexanone, acetone, ethyl methyl ketone, and methyl isobutyl ketone. Examples of the cellosolve include methyl cellosolve, methyl cellosolve acetate, ethyl cellosolve acetate, and butyl cellosolve acetate. Examples of the esters include ethyl acetate, butyl acetate, isoamyl acetate, γ-butyrolactone, and 3-methoxymethyl propionate. The above-described solvents may be used in combination of two or more thereof as necessary.

According to the type of the photosensitive composition, in order to improve the solubility, the solvent may contain dimethyl sulfoxide, N,N-dimethylformamide, N-methylpyrrolidinone, anisole, monochlorobenzene, or orthodichlorobenzene. In addition, as a low-toxic solvent, a lactic acid ester such as ethyl lactate, or propylene glycol monoethyl acetate may be used.

For the pattern formation using the photosensitive composition according to the embodiment, in the first place, the photosensitive composition is applied to a substrate to form a photosensitive layer. Any substrate may be used. Examples of the substrate include silicon wafers, doped silicon wafers, silicon wafers having various insulating films, electrodes, or wirings on their surfaces, mask blanks, and semiconductor wafers of group III-V compounds such as GaAs or AlGaAs. Alternatively, the substrate may be a chromium or chromium oxide-deposited substrate, an aluminum-deposited substrate, an IBSPG-coated substrate, an SOG-coated substrate, or an SiN-coated substrate.

Application of the photosensitive composition to the substrate may be performed by any method, for example, spin coating, dip coating, doctor blading, or curtain coating.

The applied photosensitive composition is heat-dried to form a photosensitive layer. The acid-leaving substituent of the matrix compound and the photo-acid generator are decomposed to cause reaction at high temperatures even before exposure. Therefore, the temperature of heat drying is preferably 170° C. or lower, and more preferably from 70 to 120° C.

Next, a specific region on the photosensitive layer is irradiated with actinic radiation thereby performing pattern exposure. The exposure may be performed by irradiating the photosensitive layer with actinic radiation through a specified mask pattern. Alternatively, the photosensitive layer may be directly scanned with ionizing radiation without using a mask pattern.

Any ionizing radiation for exposure may be used as long as it has a wavelength to which the photosensitive composition is sensitive. Examples of the radiation include ultraviolet radiation, i-line, h-line, or g-line from a mercury lamp, xenon lamp light, deep ultraviolet light (for example, excimer laser beams such as KrF or ArF), X rays, synchrotron orbital radiation (SR), electron beams, γ rays, and ion beams.

The exposed substrate is subjected to heat treatment (baking treatment). The heat treatment may be performed by any method. Usually, the substrate may be heated on a hot plate or in a heating furnace, or by infrared ray irradiation. In pattern formation using a chemically amplified resist composition, heat treatment is conducted to accelerate the acid-catalyst reaction, in which case the temperature during the heat treatment is preferably 150° C. or lower in order to suppress excessive diffusion of the acid.

Subsequently, the photosensitive layer is developed with an aqueous developing solution (alkaline developing solution). The alkaline developing solution may be an organic or inorganic aqueous alkaline solution. Examples of the organic aqueous alkaline solution include a tetramethyl ammonium hydroxide aqueous solution, a tetraethyl ammonium hydroxide aqueous solution and a choline aqueous solution, and examples of the inorganic aqueous alkaline solution include a potassium hydroxide aqueous solution and a sodium hydroxide aqueous solution.

The concentration of the alkaline developing solution is not limited, but is preferably 15 mol % or less to increase the difference in the rate of dissolution between the exposed and unexposed regions of the photosensitive layer thereby achieving a sufficient dissolution contrast. The concentration must be adjusted according to the amount of protecting groups introduced to the matrix compound.

As described above, the alkaline developing solution may be an aqueous developing solution having a pH of 11 or less. As necessary, the developing solution may contain any optional additives. For example, a surfactant may be added to decrease the surface tension of the developing solution, or a neutral salt may be added to activate the development. The developing solution may have an arbitrary temperature, and may be a cool or hot solution.

As necessary, the pattern formation method of the embodiment may further include other step. For example, the above-described steps may be combined with a step of forming a planarization layer before applying the photosensitive layer on the substrate, a step of forming an antireflective layer for reducing reflection of exposure light, a rinse step of washing the substrate after development treatment with water or the like thereby removing the developing solution, or a step of reirradiating the substrate with ultraviolet radiation before dry etching.

In the photosensitive layer containing the photosensitive composition according to the embodiment, the exposed regions of the photosensitive layer are selectively dissolved and removed by the development treatment, whereby a resist pattern is formed. Through the use of the photosensitive composition according to the embodiment, the method according to the embodiment forms a pattern with reduced edge roughness and high resolution and sensitivity.

Examples of the present invention will be described below.

SYNTHESIS EXAMPLE 1

50 g of phosphorus pentoxide was placed in a three-necked flask, flushed with argon, and 50 ml of dehydrated diethyl ether and 50 ml of dehydrated chloroform were added thereto. The obtained solution was stirred for 8 hours under reflux. The precipitate was removed by filtration, and the filtrate was concentrated to leave a yellow, viscous liquid product.

21.25 g of polyphosphoric acid ester and 9.25 g of 5-methoxy-1-indanone were placed in a three-necked flask, and flushed with argon. The mixture was heated to 140° C., and stirred for 2 hours under reflux. Thereafter, 50 ml of ethanol was slowly added to the flask under cooling, and stirred for 1 hour at room temperature. The precipitate was collected by suction filtration, and the precipitate was washed with acetone, and then collected.

After vacuum drying at 50° C., a yellow solid product was obtained. As a result of $^1$H-NMR measurement, the yellow product was identified as (2,7,12-trimethoxytruxene), expressed by the chemical formula shown below:

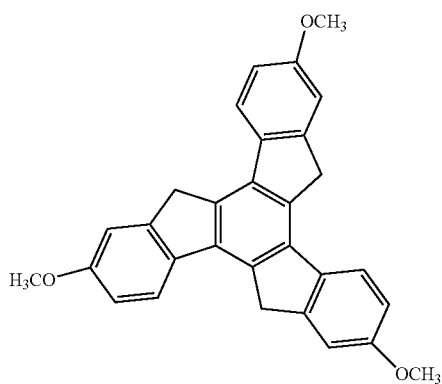

SYNTHESIS EXAMPLE 2

6.50 g of the 2,7,12-trimethoxytruxene obtained in Synthesis Example 1 was placed in a three-necked flask, and flushed with argon. 500 ml of dehydrated dimethylformamide was added to the flask, and stirred well to obtain a suspension. The suspension was cooled to 4° C., to which 1.12 g of sodium hydride, which had been washed with a small amount of dehydrated hexane, was added, and stirred to turn the color into a transparent red brown color.

Into the flask, 10.55 g of paramethoxybenzil bromide was added dropwise, and stirred for 1 hour at room temperature. Thereafter, a large amount of ethyl acetate was added, the obtained solution was washed with a dilute oxalic acid aqueous solution, and then with saturated salt water. The extracted organic layer was dried and concentrated with anhydrous sodium sulfate. The resultant residue was washed with a small amount of ethyl acetate to obtain a yellow powder product.

As a result of $^1$H-NMR measurement, the yellow product was identified as (5,10,15-tris(4-methoxyphenylmethyl)-2,7,12-trimethoxytruxene), expressed by the chemical formula shown below:

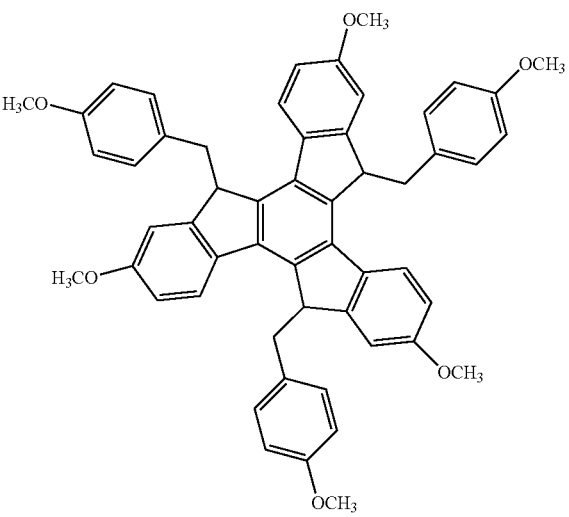

SYNTHESIS EXAMPLE 3

3 g of the 5,10,15-tris(4-methoxyphenylmethyl)-2,7,12-trimethoxytruxene obtained in Synthesis Example 2 was placed in a three-necked flask, and flushed with argon. Into the flask, 500 ml of 30% hydrogen bromide-containing acetic acid solution was added, and allowed to react for 2 hours under reflux. The reaction mixture was added to a large amount of ice water, and the resultant solid was collected, and washed with pure water.

The collected solid was dissolved in ethyl acetate, washed twice with pure water, twice with a 5% sodium hydrogen carbonate aqueous solution, and then again with pure water. The extracted organic layer was dried and concentrated with anhydrous magnesium sulfate to obtain a yellow powder product.

As a result of $^1$H-NMR measurement, the yellow product was identified as (5,10,15-tris(4-hydroxyphenylmethyl)-2,7,12-trihydroxytruxene (hereinafter referred to as THBTX) expressed by the chemical formula shown below:

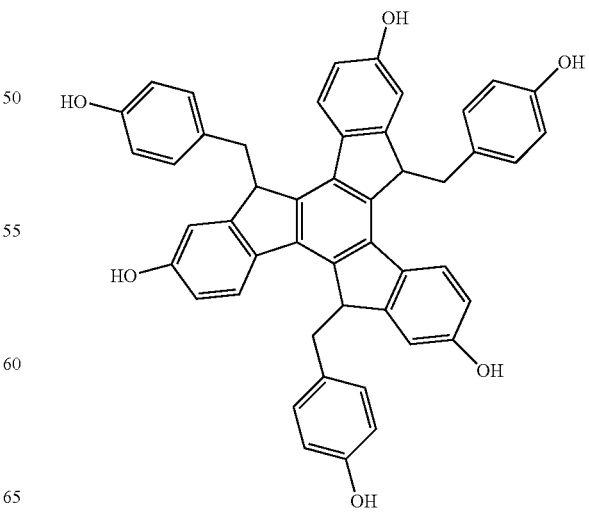

SYNTHESIS EXAMPLE 4

0.213 g of the THBTX obtained in Synthesis Example 3 was placed in a three-necked flask, and dissolved in 3.0 g of ethyl acetate. 0.79 g of adamantyl ethyl vinyl ether was added and stirred, and then 0.014 g of dichloroacetic acid was added dropwise, and stirred.

The solution, after leaving overnight, was added to 6.0 g of a 0.5% sodium hydroxide aqueous solution, and extracted three times with ethyl acetate. The ethyl acetate solution was washed with pure water, concentrated, and precipitated with hexane. The precipitate was collected, and dried to obtain a yellow powder product. The yield was 0.34 g.

As a result of $^1$H-NMR measurement, the yellow product was identified as (partially protected 5,10,15-tris(4-adamantylethyloxyethoxyphenylmethyl)-2,7,12-adamantylethyloxyethoxytruxene (hereinafter referred to as AEVEBTX), expressed by the chemical formula shown below:

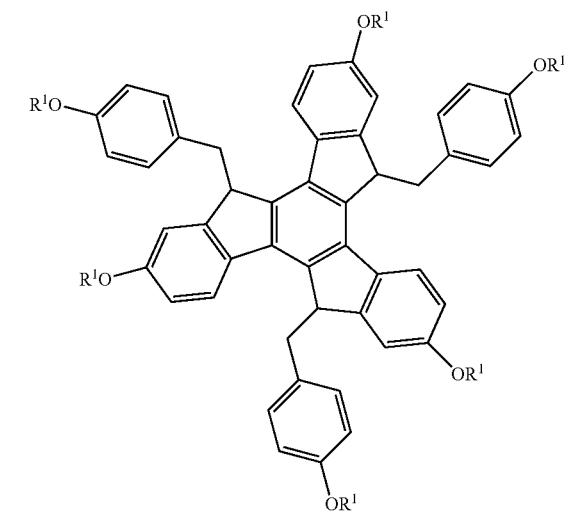

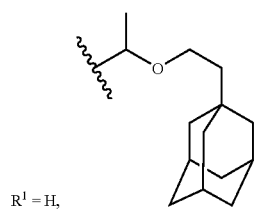

$R^1 = H$,

SYNTHESIS EXAMPLE 5

0.213 g of the THBTX obtained in Synthesis Example 3 was placed in a three-necked flask, and dissolved in 3.0 g of ethyl acetate. 0.75 g of hyper-lactone vinyl ether was added and stirred, and then 0.014 g of dichloroacetic acid was added dropwise, and stirred.

The solution, after leaving overnight, was added to 6.0 g of a 0.5% sodium hydroxide aqueous solution, and extracted three times with ethyl acetate. The ethyl acetate solution was washed with pure water, concentrated, and precipitated with hexane. The precipitate was collected, and dried to obtain a yellow powder product. The yield was 0.26 g.

As a result of $^1$H-NMR measurement, the yellow product was identified as (partially protected 5,10,15-tris(4-hyper lactyloxyethyloxyphenylmethyl)-2,7,12-hyper lactyloxyethyloxytruxene (hereinafter referred to as HPVEBTX) expressed by the chemical formula shown below:

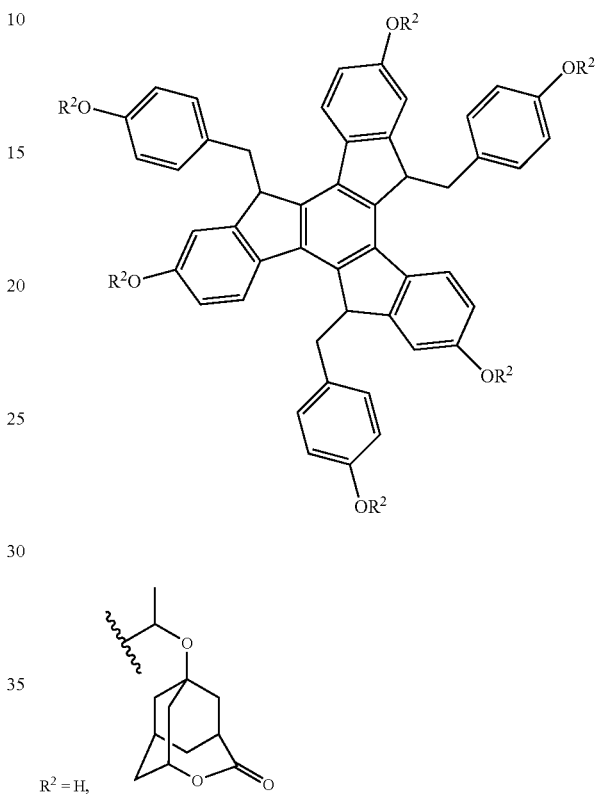

$R^2 = H$,

SYNTHESIS EXAMPLE 6

0.213 g of the THBTX obtained in Synthesis Example 3 was placed in a three-necked flask, and dissolved in 3.0 g of ethyl acetate. 0.375 g of hyper-lactone vinyl ether and 0.371 g of adamantyl ethyl vinyl ether were added and stirred, and then 0.014 g of dichloroacetic acid was added dropwise, and stirred.

The solution after a lapse of overnight was added to 6.0 g of a 0.5% sodium hydroxide aqueous solution, and extracted three times with ethyl acetate. The ethyl acetate solution was washed with pure water, concentrated, and precipitated with hexane. The precipitate was collected, and dried to obtain a yellow powder product. The yield was 0.30 g.

As a result of $^1$H-NMR measurement, the yellow product was identified as (partially protected 5,10,15-tris(4-adamantylethoxy/hyper lactyloxyethyloxyphenylmethyl)-2,7,12-adamantylethoxy/hyper lactyloxyethyloxytruxene (hereinafter referred to as AEVE-HPVEBTX), expressed by the chemical formula shown below:

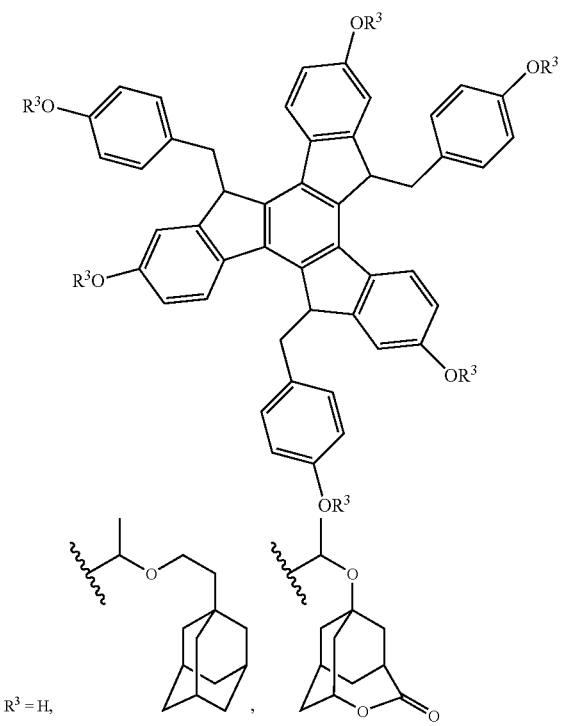

The compounds having a truxene structure were synthesized as described above. These compounds were dissolved in methoxymethyl propionate as a solvent, to which a photo-acid generator and a basic compound were added to prepare a resist solution. The photo-acid generator was triphenyl sulfonium triflate, and the basic compound was tributylamine.

The formulation of the resist solution is shown in Table 1. In Table 1, the values represent the content. In the following Examples and Comparative Examples, the content of the matrix compound is percentage by weight with respect to the solvent, and the content of the photo-acid generator is percentage by weight with respect to the matrix compound. The content of the basic compound is percentage by mole with respect to the photo-acid generator.

TABLE 1

| Resist solution | Matrix compound | Photo-acid generator | Basic compound |
| --- | --- | --- | --- |
| 1 | AEVEBTX | 1 | 0 |
| 2 | AEVEBTX | 1 | 5 |
| 3 | HPVEBTX | 1 | 0 |
| 4 | HPVEBTX | 1 | 5 |
| 5 | AEVE-HPVEBTX | 1 | 0 |
| 6 | AEVE-HPVEBTX | 1 | 5 |

EXAMPLES 1 to 6

Resist films were formed using the resist solutions prepared as described above, and a pattern was formed. Specifically, the resist solution was applied to the silicon wafer by spin coating, thereby forming a resist film having a thickness of about 200 nm. The obtained resist film was baked at 110° C. for 90 seconds, and then subjected to pattern exposure using a KrF excimer laser stepper.

As necessary, a baking treatment was performed after exposure, and development was performed with a tetramethyl ammonium hydroxide (TMAH) aqueous solution to form a positive pattern. The presence or absence of pattern peeling was observed with SEM, and the adhesion was rated according to the following criteria. The rates "○" and "Δ" are acceptable levels of adhesion.

○: No peeling occurred.
Δ: Peeling occurred.
×: The pattern was completely peeled off, and did not remain in the predetermined position.

The treatment conditions are shown in Table 2, and the results are summarized in Table 3.

TABLE 2

| Example | Resist solution | Post exposure bake (temperature/time) | Development (concentration/time) |
| --- | --- | --- | --- |
| 1 | 1 | 110° C./90 seconds | 2.38%/30 seconds |
| 2 | 2 | 110° C./90 seconds | 2.38%/30 seconds |
| 3 | 3 | 110° C./90 seconds | 2.38%/30 seconds |
| 4 | 4 | 110° C./90 seconds | 2.38%/30 seconds |
| 5 | 5 | 110° C./90 seconds | 2.38%/30 seconds |
| 6 | 6 | 110° C./90 seconds | 2.38%/30 seconds |

TABLE 3

| Example | Sensitivity (mJ/cm$^2$) | Resolution (μm) | Adhesion |
| --- | --- | --- | --- |
| 1 | 10.0 | 0.3 | ○ |
| 2 | 12.0 | 0.3 | ○ |
| 3 | 5.2 | 0.3 | ○ |
| 4 | 6.0 | 0.3 | ○ |
| 5 | 7.0 | 0.3 | ○ |
| 6 | 8.0 | 0.3 | ○ |

As is evident from the results in Tables 2 and 3, all the photosensitive compositions according to the embodiment are capable of forming a fine pattern by alkaline development. In consideration of the photosensitive mechanism of the photo-acid generator, it is readily estimated that all the photosensitive compositions are photosensitive to EUV light, or soft X rays (13 nm). More specifically, the photosensitive composition according to the embodiment is applicable to future EUV lithography.

Next, a resist solution was prepared according to the formulation shown in Table 4. The photo-acid generator was triphenyl sulfonium triflate, and the basic compound was tributylamine.

TABLE 4

| Resist solution | Matrix compound | Photo-acid generator | Basic compound |
| --- | --- | --- | --- |
| 7 | AEVEBTX | 5 | 10 |
| 8 | AEVEBTX | 5 | 30 |
| 9 | HPVEBTX | 5 | 10 |
| 10 | HPVEBTX | 5 | 30 |
| 11 | AEVE-HPVEBTX | 5 | 30 |
| 12 | AEVE-HPVEBTX | 5 | 80 |

EXAMPLES 7 to 12

An electron beam writing test was conducted using the resist solutions 7 to 12. Specifically, the resist solution was applied to a silicon wafer by spin coating to form a resist film having a thickness of about 100 nm. The obtained resist film was baked at 110° C. for 90 seconds, and subjected to pattern lithography with a low-energy electron-beam writing system (accelerating voltage of electron beams: 5 keV).

As necessary, a baking treatment was performed after exposure, and development was performed with a tetramethyl ammonium hydroxide (TMAH) aqueous solution to form a positive pattern. The treatment conditions are shown in Table 5, and the results are summarized in Table 6.

TABLE 5

| Example | Resist solution | Post exposure bake (temperature/time) | Development (concentration/time) |
|---|---|---|---|
| 7 | 7 | 110° C./90 seconds | 2.38%/30 seconds |
| 8 | 8 | 110° C./90 seconds | 2.38%/30 seconds |
| 9 | 9 | 110° C./90 seconds | 2.38%/30 seconds |
| 10 | 10 | 110° C./90 seconds | 2.38%/30 seconds |
| 11 | 11 | 110° C./90 seconds | 2.38%/30 seconds |
| 12 | 12 | 110° C./90 seconds | 2.38%/30 seconds |

TABLE 6

| Example | Sensitivity (μC/cm$^2$) | Roughness (nm) | Adhesion |
|---|---|---|---|
| 7 | 1.99 | 8 | Δ |
| 8 | 3.74 | 6 | Δ |
| 9 | 0.2 | 10 | Δ |
| 10 | 0.7 | 9 | Δ |
| 11 | 1.4 | 7 | ○ |
| 12 | 2.45 | 5 | ○ |

The roughness was evaluated based on the evaluation of line width roughness (LWR). The resist film was subjected to electron beam lithography, baking treatment, and development treatment with a TMAH aqueous solution to form a line-and-space pattern with a line width of 100 nm. The LWR value (3 σ value) of the obtained pattern was calculated within the range of 350 nm×200 nm (ROI).

As is evident from the results in Table 5, all of the photo-sensitive compositions according to the embodiment are developable with an aqueous alkaline solution. In particular, the results of the adhesion test shown in Table 6 indicate that a pattern which very favorably adheres to the substrate was provided when AEVE-HPVEBTX was used as the matrix compound (EXAMPLES 11 and 12). In addition, the results shown in Table 6 indicate that a resist pattern with a roughness reduced to within acceptable tolerance limits and a high sensitivity is formed, which result in excellent resolution.

COMPARATIVE EXAMPLE 1

1.50 g of the THBTX obtained in Synthesis Example 3 was placed in a three-necked flask, and dissolved in 50 ml of dehydrated tetrahydrofuran. 5.09 g of potassium carbonate, 6.45 g of 18-crown-6, and 7.46 ml of pyrocarboxylic acid di-t-butyl dicarbonate were added in this order under stirring.

After stirring at 40° C. for 1 hour, pure water was added. The organic layer was extracted with ethyl acetate three times, and the layer was concentrated, purified by silica gel column chromatography (developing solvent: ethyl acetate), and recrystallized with tetrahydrofuran. The obtained solid was dried by suction filtration to obtain a yellow powder product. The yield was 0.50 g.

As a result of $^1$H-NMR measurement, the yellow product was identified as partially protected 5,10,15-tris(4-t-butoxy-carbonyloxyphenylmethyl)-2,7,12-trit-butoxycarbonylox-ytruxene (hereinafter referred to as TBOBTX) expressed by the chemical formula shown below:

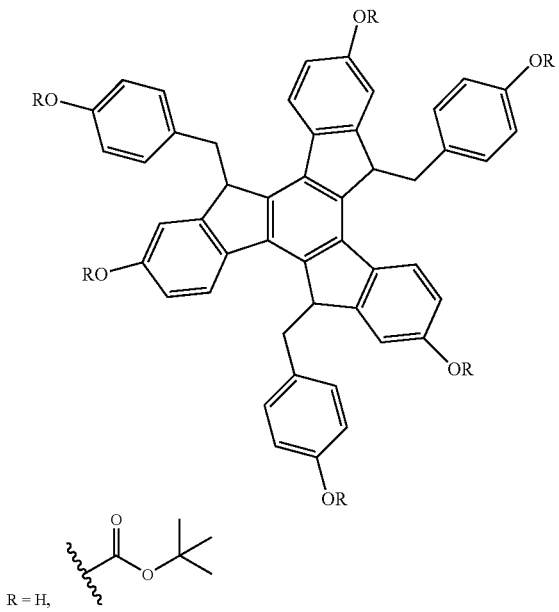

Using the TBOBTX as the matrix compound, a resist solution 13 was prepared according to the formulation shown in Table 7. The photo-acid generator was triphenyl sulfonium triflate, and the basic compound was tributylamine.

TABLE 7

| Resist solution | Matrix compound | Photo-acid generator | Basic compound |
|---|---|---|---|
| 13 | TBOBTX | 5 | 30 |

The electron beam lithography test was performed in the same manner as Examples to examine the sensitivity and adhesion. The treatment conditions are shown in Table 8, and the results are summarized in Table 9. For comparison, the results of Example 11 are also shown in these tables.

TABLE 8

| Example | Resist solution | Post exposure bake (temperature/time) | Development (concentration/time) |
|---|---|---|---|
| Example 11 | 11 | 110° C./90 seconds | 2.38%/30 seconds |
| Comparative Example 1 | 13 | 110° C./90 seconds | 2.38%/30 seconds |

TABLE 9

| Example | Sensitivity (μC/cm$^2$) | Adhesion |
|---|---|---|
| Example 11 | 1.4 | ○ |
| Comparative Example 1 | 5.6 | X |

As is evident from the results shown in Table 9, the photo-sensitive composition of the Example containing, as the matrix compound, the truxene compound having a specific acid-leaving group formed a pattern with a higher sensitivity than the photosensitive composition of the Comparative Example. This is because the acetal bond is readily cleaved by the acid generated. In addition, the composition has an alicyclic structure, which makes the latent image before development scarcely visible, and produces little outgas.

COMPARATIVE EXAMPLE 2

Using a partially t-butoxycarbonyloxy substituted polyhydroxystyrene having a molecular weight of 20000 (hereinafter referred to as TBOPHS) as the matrix compound, a resist solution 14 was prepared according to the formulation shown in Table 10. The photo-acid generator was triphenyl sulfonium triflate, and the basic compound was tributylamine.

TABLE 10

| Resist solution | Matrix compound | Photo-acid generator | Basic compound |
|---|---|---|---|
| 14 | TBOPHS | 5 | 30 |

The electron beam lithography test was performed in the same manner as Examples to examine the roughness and adhesion. The treatment conditions are shown in Table 11, and the results are summarized in Table 12. For comparison, the results of Example 11 are also shown in these tables. A 500 nm×500 nm region of the surface thereof was measured with an AFM measuring instrument (Nanoscope III, tapping mode, with a super sharp silicon chip [SSS-NCH-50] used in a cantilever) to evaluate its surface roughness (Ra value) in a 250 nm×250 nm region with analysis software attached to the AFM measuring instrument. The results thus obtained are summarized in Table 12.

TABLE 11

| Example | Resist solution | Post exposure bake (temperature/time) | Development (concentration/time) |
|---|---|---|---|
| Example 11 | 11 | 110° C./90 seconds | 2.38%/30 seconds |
| Comparative Example 2 | 14 | 110° C./90 seconds | 2.38%/30 seconds |

TABLE 12

| Example | Surface roughness (nm) | Adhesion |
|---|---|---|
| Example 11 | 0.96 | ○ |
| Comparative Example 2 | 3.03 | ○ |

As is evident from the results shown in Table 12, the photosensitive composition of the Example containing, as the matrix compound, the truxene compound having a specific acid-leaving group exhibited a smaller roughness than the photosensitive composition of the Comparative Example. This is because the average molecular weight of TBOPHS is 20000, while the molecular weight of the truxene compound is as small as 1000 to 2000.

COMPARATIVE EXAMPLE 3

2 g of 1,3,5-tris(4-hydroxyphenyl)benzene was placed in a three-necked flask, and flushed with argon. 50 ml of dehydrated tetrahydrofuran was added into the flask to dissolve the substrate. Under stirring the solution, 7.52 g of potassium carbonate, 9.52 g of 18-crown-6, and 11.05 ml of pyrocarboxylic acid di-t-butyl dicarbonate were added in this order.

After stirring at 40° C. for 10 hours, pure water was added. The organic layer was extracted with ethyl acetate three times, and the layer was concentrated, purified by silica gel column chromatography (developing solvent: ethyl acetate), and recrystallized with a tetrahydrofuran-methanol mixed solvent. The obtained solid was dried by suction filtration to obtain a white powder product.

As a result of $^1$H-NMR measurement, the white powder product was identified as 1,3,5-tris(4-t-butoxycarbonyloxyphenyl)benzene (hereinafter referred to as TBOTPB) expressed by the chemical formula shown below:

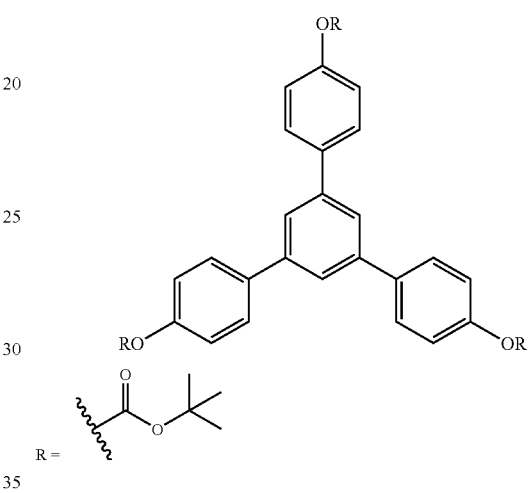

Using the TBOTPB as the matrix compound, a resist solution 15 was prepared according to the formulation shown in Table 13. The photo-acid generator was triphenyl sulfonium triflate, and the basic compound was tributylamine.

TABLE 13

| Rsist solution | Matrix compound | Photo-acid generator | Basic compound |
|---|---|---|---|
| 15 | TBOTPB | 5 | 30 |

The electron beam lithography test was performed in the same manner as Examples to examine the sensitivity and adhesion. The treatment conditions are shown in Table 14, and the results are summarized in Table 15. For comparison, the results of Example 11 are also shown in these tables. The surface roughness was measured in the same manner as Examples.

TABLE 14

| Example | Resist solution | Post exposure bake (temperature/time) | Development (concentration/time) |
|---|---|---|---|
| Example 11 | 11 | 110° C./90 seconds | 2.38%/30 seconds |
| Comparative Example 3 | 15 | 110° C./90 seconds | 2.38%/30 seconds |

25

TABLE 15

| Example | Sensitivity (μC/cm²) | Surface roughness (nm) | Adhesion |
|---|---|---|---|
| Example 11 | 1.4 | 0.96 | ○ |
| Comparative Example 3 | 6.4 | 1.30 | X |

As is evident from the results shown in Table 15, the photosensitive composition of the Example containing, as the matrix compound, the truxene compound having a specific acid-leaving group formed a pattern with a higher sensitivity, and exhibited a smaller roughness than the photosensitive composition of the Comparative Example. The obtained pattern also exhibited a favorable adhesion to the substrate. The improvement of sensitivity is owing to easy cleavage of the acetal bond by the acid, and the improvement of roughness is owing to the small molecular size of the truxene compound. In addition, the improvement of the adhesion to the substrate is owing to the rigid structure and small entanglement between molecular chains.

On the other hand, TBOTPB exhibited a lower sensitivity because it is difficult for the acid to cleave the carboxy ether bond in the acid-leaving group. In addition, the obtained pattern exhibited poor roughness and adhesion due to the fact that the compound has a softer structure than truxene, entanglement between the molecular chains is strong, and the glass transition temperature is as low as about 70° C.

As described above, the photosensitive composition according to the embodiment is capable of forming a resist pattern with reduced roughness under future EUV lithography, and provides a great industrial value.

The alkaline-developable photosensitive composition adaptable to fine patterns is provided.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A photosensitive composition comprising:
a compound expressed by the formula T1:

formula T1

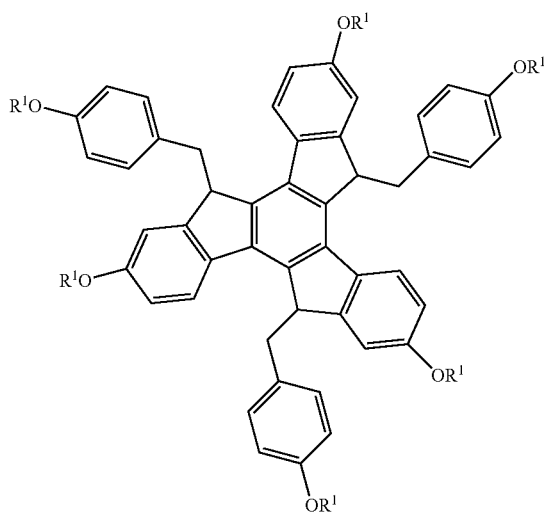

26 wherein $R^1$s are hydrogen atoms, and are partially substituted with hydrophobic groups, the hydrophobic groups being at least one selected from the group consisting of AD-1, AD-2, and AD-3 shown below; and

AD-1

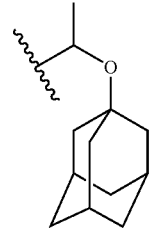

AD-2

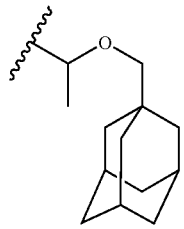

AD-3

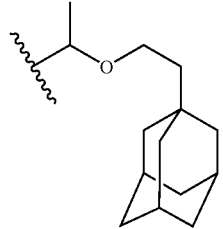

a photo-acid generator which generates an acid by an action of actinic radiation.

2. The composition according to claim 1, wherein the hydrogen atoms constitute 10 to 90% of the total number of $R^1$s.

3. The composition according to claim 1, wherein the hydrogen atoms constitute 20 to 60% of the total number of $R^1$s.

4. The composition according to claim 1, wherein the hydrophobic groups include at least the hydrophobic group AD-3.

5. The composition according to claim 1, further comprising a basic compound.

6. A photosensitive composition comprising:
a compound expressed by the formula T2:

formula T2

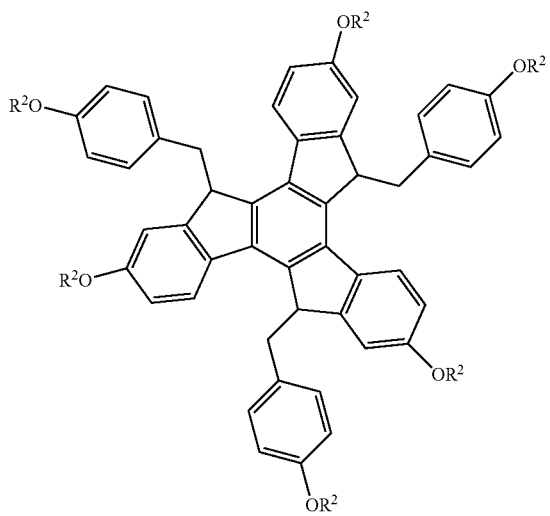

wherein R²s are hydrogen atoms, and are partially substituted with a hydrophilic group LA shown below; and

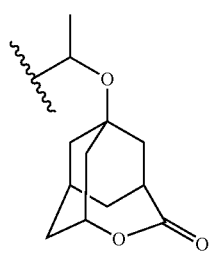

LA a photo-acid generator which generates an acid by an action of actinic radiation.

7. The composition according to claim 6, wherein the hydrogen atoms constitute 10 to 90% of the total number of R²s.

8. The composition according to claim 6, wherein the hydrogen atoms constitute 60 to 80% of the total number of R²s.

9. The composition according to claim 6, further comprising a basic compound.

10. A photosensitive composition comprising:
a compound expressed by the formula T3:

formula T3

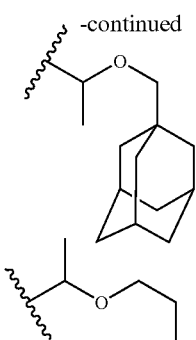

wherein R³s are hydrogen atoms and hydrophobic groups, the hydrophobic groups being selected from the group consisting of AD-1, AD-2, and AD-3 shown below, the hydrogen atoms being partially substituted with a hydrophilic group LA shown below; and

AD-1

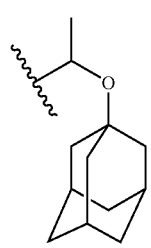

-continued

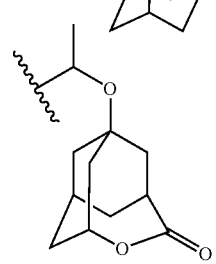

AD-2

AD-3

LA a photo-acid generator which generates an acid by an action of actinic radiation.

11. The composition according to claim 10, wherein the hydrogen atoms constitute 10 to 90% of the total number of R³s.

12. The photosensitive composition according to claim 10, wherein the hydrogen atoms constitute 40 to 80% of the total number of R³s.

13. The composition according to claim 10, wherein a ratio between the hydrophobic and hydrophilic groups is from 2:1 to 1:2.

14. The composition according to claim 10, wherein a ratio between the hydrophobic and hydrophilic groups is from 2:3 to 3:2.

15. The composition according to claim 10, wherein a ratio between the hydrophobic and hydrophilic groups is 1:1.

16. The composition according to claim 10, wherein the hydrophobic groups include at least the hydrophobic group AD-3.

17. The composition according to claim 10, further comprising a basic compound.

18. A method for forming a pattern, comprising:
forming a photosensitive layer containing the photosensitive composition of claim 1 above a substrate;
subjecting a predetermined region of the photosensitive layer to pattern exposure by irradiation with actinic radiation;
subjecting the substrate to a heat treatment; and
subjecting the photosensitive layer after the heat treatment to a development treatment with an alkali aqueous solution, to selectively remove the light-exposed portion of the photosensitive layer.

19. A method for forming a pattern, comprising:
forming a photosensitive layer containing the photosensitive composition of claim 6 above a substrate;

subjecting a predetermined region of the photosensitive layer to pattern exposure by irradiation with actinic radiation;

subjecting the substrate to a heat treatment; and subjecting the photosensitive layer after the heat treatment to a development treatment with an alkali aqueous solution, to selectively remove the light-exposed portion of the photosensitive layer.

20. A method for forming a pattern, comprising:

forming a photosensitive layer containing the photosensitive composition of claim 10 above a substrate;

subjecting a predetermined region of the photosensitive layer to pattern exposure by irradiation with actinic radiation;

subjecting the substrate to a heat treatment; and subjecting the photosensitive layer after the heat treatment to a development treatment with an alkali aqueous solution, to selectively remove the light-exposed portion of the photosensitive layer.

* * * * *